United States Patent
Schmuck et al.

(10) Patent No.: US 9,339,319 B2
(45) Date of Patent: May 17, 2016

(54) SURGICAL REDUCTION CLAMP

(71) Applicant: Stryker Leibinger GmbH & Co. KG, Freiburg (DE)

(72) Inventors: Manfred Schmuck, Muehlheim-Stetten/Donau (DE); Denis Digeser, Freiburg (DE); Uwe Koerner, Muehlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 257 days.

(21) Appl. No.: 13/949,881

(22) Filed: Jul. 24, 2013

(65) Prior Publication Data

US 2014/0031882 A1  Jan. 30, 2014

(30) Foreign Application Priority Data

Jul. 25, 2012 (EP) .................................... 12005423

(51) Int. Cl.
 *A61B 17/68* (2006.01)
 *A61B 17/88* (2006.01)
 *A61B 17/28* (2006.01)
 *A61B 17/00* (2006.01)

(52) U.S. Cl.
 CPC ......... *A61B 17/8866* (2013.01); *A61B 17/2804* (2013.01); *A61B 17/68* (2013.01); *A61B 17/282* (2013.01); *A61B 17/2816* (2013.01); *A61B 2017/0069* (2013.01); *A61B 2017/00407* (2013.01); *A61B 2017/00473* (2013.01); *A61B 2017/2837* (2013.01)

(58) Field of Classification Search
 CPC ..... A61B 17/68; A61B 17/8866; A61B 17/66
 See application file for complete search history.

(56) References Cited

U.S. PATENT DOCUMENTS

| | | | | |
|---|---|---|---|---|
| 2,181,746 A | * | 11/1939 | Siebrandt | A61B 17/17 408/115 R |
| 2,250,417 A | * | 7/1941 | Ettinger | A61B 17/60 606/54 |
| 4,896,661 A | | 1/1990 | Bogert et al. | |
| 5,921,985 A | * | 7/1999 | Ross, Jr. | A61B 17/6466 606/54 |
| 5,944,723 A | * | 8/1999 | Colleran | A61B 17/8866 606/208 |
| 6,716,218 B2 | | 4/2004 | Holmes et al. | |
| 7,758,651 B2 | | 7/2010 | Chauhan et al. | |

(Continued)

FOREIGN PATENT DOCUMENTS

| | | |
|---|---|---|
| CN | 2412535 Y | 1/2001 |
| CN | 202154736 U | 3/2012 |

(Continued)

OTHER PUBLICATIONS

Extended European Search Report for Application No. EP12005423 dated Oct. 15, 2012.

*Primary Examiner* — Christian Sevilla
(74) *Attorney, Agent, or Firm* — Lerner, David, Littenberg, Krumholz & Mentlik, LLP

(57) ABSTRACT

A surgical reduction clamp has a first clamping arm and a second clamping arm movable relative to the first clamping arm. The first clamping arm comprises a base portion, a tip portion, a joint movably coupling the tip portion to the base portion, and a locking member adapted to lock the joint so as to fasten a position of the tip portion relative to the base portion. The joint is a revolute joint having a spherical portion which can be locked into position by a clamping force.

16 Claims, 4 Drawing Sheets

(56) References Cited

U.S. PATENT DOCUMENTS

| | | |
|---|---|---|
| 8,216,242 B2 | 7/2012 | Marchyn et al. |
| 2011/0224734 A1 | 9/2011 | Schelling |
| 2012/0095473 A1 | 4/2012 | Soliman et al. |

FOREIGN PATENT DOCUMENTS

| | | | |
|---|---|---|---|
| WO | 89/06939 A1 | 8/1989 | |
| WO | 9925262 A1 | 5/1999 | |
| WO | WO 9925262 A1 * | 5/1999 | ......... A61B 17/7077 |

* cited by examiner

SURGICAL REDUCTION CLAMP

CROSS-REFERENCE TO RELATED APPLICATION

The present application claims priority from European Patent Application No. 12 005 423.4 filed Jul. 25, 2012, the disclosure of which is hereby incorporated herein by reference.

BACKGROUND OF THE INVENTION

The present disclosure generally relates to the field of surgical instruments. In particular, a surgical reduction clamp is described.

When treating a bone fracture, bone fragments are typically aligned in a first step. The act of aligning and restoring the correct position of bone fragments is called reduction. Perfect anatomical reduction reverses the mechanism of injury which originally created the fracture displacement.

In a surgical procedure, often a screw, plate, pin or wire is installed across a fracture in order to maintain the alignment of the bone fragments for the later adhesion process. During the installation procedure, it is in many cases important to clamp the bone fragments together so as to eliminate the existence of gaps which may potentially reduce the chances of proper adhesion.

Various types of reduction clamps are available for such osteosynthesis procedures. Many of them are limited in their practical applicability for certain surgical treatments due to insufficient usability characteristics from the perspective of the operating surgeon.

WO 89/06939 A1 discloses a multi-purpose clamping forceps for use in orthopedic surgical procedures. The forceps has interchangeable tip elements and a reversible ratchet mechanism for controlling the tip elements. A variety of tip elements is provided and can be used for compression and distraction of plate and screw fixation systems as well as gripping and manipulating the bone.

WO 99/25262 A1 discloses a surgical tool for bone manipulation with a pair of pivotably connected handles. Joints provided at the ends of the handles are pivotably connected to respective attachment devices for engaging implants placed in a bone. A ratchet pivotably mounted to the first handle is engageable with the second handle.

However, such instruments are still not applicable in many surgical situations and usability aspects may still be improved.

BRIEF SUMMARY OF THE INVENTION

Accordingly, there is a need for a surgical reduction clamp which provides improved usability and which is easy to handle.

A surgical reduction clamp comprising a first clamping arm and a second clamping arm movable relative to the first clamping arm is provided. The first clamping arm comprises a base portion, a tip portion, a joint movably coupling the tip portion to the base portion, and a locking member adapted to lock the joint so as to fasten a position of the tip portion relative to the base portion.

The tip portion may form the proximal end of the first clamping arm and represent that portion of the first clamping arm that engages the human anatomy when applied in a surgical procedure. Alternatively, or in addition, the tip portion may engage surgical devices or implants applied during a treatment, such as a surgical wire. The tip portion may comprise a sharp bone tip to grip a bone, a sleeve to accommodate a surgical wire or another elongate member, or any other type of surgical instrument tip design.

The base portion may form the distal end of the first clamping arm and may be formed as an integral part thereof. The base portion may generally represent that part of the first clamping arm that may be used by the operating surgeon for gripping the reduction clamp so as to properly operate the clamp as required during the procedure.

Any type of structure allowing a movable relationship between the first and the second clamping arm so as to enable for a clamping capability between the first and the second arm may generally be used. The first and the second clamping arm may, for example, be coupled in a pivotable relationship relative to one another, hence, forming a forceps or pincers. In other implementations the first and the second clamping arm may be movable relative to each other in a translatory manner.

The tip portion of the first clamping arm may be movably coupled to the base portion of the first clamping arm. For certain applications, it may be desired to rotatably couple the tip portion to the base portion. In this way, the tip portion may be rotated relative to the base portion, and the joint member may be a revolute joint. The rotational direction may generally be orientated in any direction relative to the first clamping arm. The rotation may be limited about a longitudinal axis of the first clamping arm. A longitudinal axis of the tip portion may extend substantially perpendicularly to a longitudinal axis of the first clamping arm.

It will be understood that alternative or additional types of coupling the tip portion to the base portion are conceivable. The joint may, for example, pivotably couple the tip portion to the base portion, thus, allowing a pivoting movement of the tip portion relative to the base portion. A pivoting and a rotational coupling may also be combined so that a pivoting movement about a pivot axis and a rotational movement about a longitudinal axis of the first clamping arm are allowed at the same time. Such behavior may be realized by coupling the tip portion to the base portion by means of, for example, a ball joint.

The position of the tip portion relative to the base portion may be fixed by locking the joint using a locking mechanism realized by the locking member. The locking member may be adapted to lock the joint by applying a clamping force. For this purpose, bearing members of the joint may be clamped together by the locking member. The joint may for example comprise two opposed bearing members exhibiting a clearance in between serving to receive and clamp a part of the tip portion, such as its distal end. The locking member may also be adapted to release the joint for loosening the clamping force again. The locking mechanism for creating or loosening the clamping force may comprise a screw-nut mechanism.

The locking member may comprise a handle for actuation by the operating surgeon. Placing or turning the handle into a locking position or direction, respectively, may create the clamping force to lock the joint. Placing or turning the handle into a release position or direction, respectively, may loosen the clamping force and release the joint. As an alternative, the locking member may also comprise a screw head for actuating the locking member. The screw head may serve for the same purpose as the handle described above.

The joint may further be adapted to allow the tip portion to be releasable from the base portion, thus, making the tip portion interchangeable. A sleeve tip may for example be exchanged by a sharp bone tip, or vice versa.

A spring may be provided between the first clamping arm and the second clamping arm so as to bias the first clamping arm and the second clamping arm relative to one another. The bias may be selected so as to support the surgeon operating the reduction clamp. The bias may, for example, establish a force pushing the tip portions of the clamping arms away from each other.

Further, a ratchet toothed member or any other mechanism may extend from one of the first and the second clamping arm towards the other clamping arm so as to permit locking of the position of the first and the second clamping arm relative to one another (e.g., by engagement of the other clamping arm with the teeth of the ratchet toothed member). The ratchet toothed member may particularly act jointly with the spring in that the spring bias forces the one clamping arm into the teeth of the ratchet toothed member, thus, preventing the one clamping arm from slipping out of the teeth it engages with.

Further realizations of the surgical reduction clamp may be defined by the configuration of the second clamping arm. The second clamping arm may generally exhibit the same configuration as the first clamping arm. The second clamping arm may also comprise a base portion, a tip portion, a joint movably coupling the tip portion to the base portion of the second clamping arm, and a locking member adapted to lock the joint so as to fasten a position of the tip portion relative to the base portion of the second clamping arm. Further, the second clamping arm may comprise a tip portion that is integrally joined to the base portion of the second clamping arm. In any of these cases, the tip portion of the second clamping arm may comprise a sleeve, a sharp bone tip, or any other type of surgical instrument tip design.

BRIEF DESCRIPTION OF THE DRAWINGS

Further details, advantages and aspects of the present disclosure will become apparent from the following description of exemplary embodiments taken in conjunction with the drawings, wherein.

DETAILED DESCRIPTION

Figure 1:
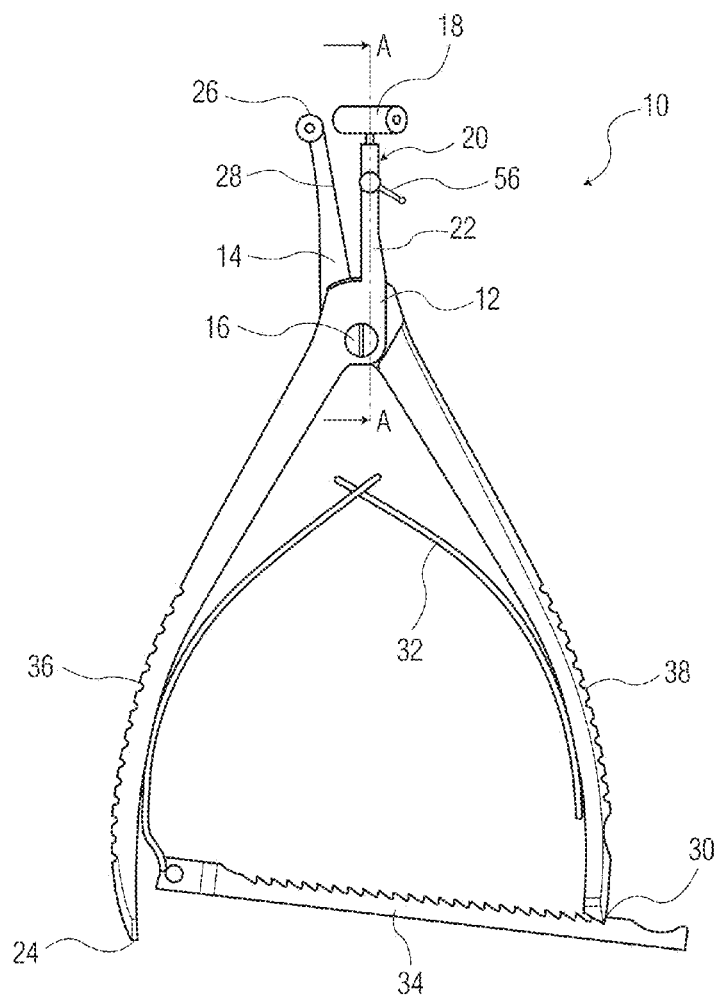
FIG. 1 shows a side view of the surgical reduction clamp according to an embodiment of the present disclosure.

In the following, various embodiments of a surgical reduction clamp will be described. The same reference numerals will be used to denote the same or similar structural features.

FIG. 1 shows a side view of an embodiment of a surgical reduction clamp 10. The reduction clamp 10 comprises a first clamping arm 12 and a second clamping arm 14 which are pivotably coupled to one another by a screw or bolt member 16. The first clamping arm 12 includes a tip portion 18 forming its proximal end. In FIG. 1, the tip portion 18 is formed as a sleeve for accommodating a surgical wire, such as a k-wire. The tip portion 18 is coupled to a joint 20 and the joint 20, in turn, adjoins a base portion 22 of the first clamping arm 12 which extends to the distal end 24 thereof.

As opposed to the first clamping arm 12, the second clamping arm 14 does not include a joint. The second clamping arm 14 only includes a tip portion 26 forming its proximal end and a base portion 28 integrally adjoining the tip portion 26 and extending to the distal end 30 of the second clamping arm 14.

Similar to the tip portion 18 of the first clamping arm 12, the tip portion 26 of the second clamping arm 14 is formed as a sleeve.

By pivotably coupling the first clamping arm 12 to the second clamping arm 14 in the manner as depicted in FIG. 1, the reduction clamp 10 takes the shape of a forceps. When pushing the distal ends 24 and 30 of the first and the second clamping arm 12 and 14 together, the tip portions 18 and 26 of the first and the second clamping arm 12 and 14 undergo a pivoting movement about member 16 and are also pushed towards each other at their proximal ends. In this way, a clamping capability between the tip portions 18 and 26 is provided which allows the operating surgeon to align bone fragments in a surgical procedure with the help of, for example, k-wires.

It will be understood that the tip portions 18 and 26 may comprise any other kind of surgical instrument tip design instead of the illustrated sleeves 18 and 26. It will further be understood that the first and the second clamping arms 12 and 14 do not necessarily have to be coupled in the forceps-like manner as illustrated in FIG. 1. Any other type of movable relationship (e.g., in a translatory manner) between a first and a second clamping arm providing a clamping capability between their tip portions could likewise be implemented.

A leg spring 32 is disposed between the first clamping arm 12 and the second clamping arm 14 providing a bias that pushes the distal ends 24 and 30 of the first and the second clamping arm 12 and 14 away from each other. Due to the pivotable coupling of the first and the second clamping arm 12 and 14 by means of the member 16, this bias forces the tip portions 18 and away from each other. The bias particularly improves the handling of the reduction clamp 10 and assists the operating surgeon in operating the reduction clamp during a surgical procedure. Any other type of spring may be employed to establish a bias force between the first and the second clamping arm 12 and 14.

Further, a ratchet toothed member 34 is shown in FIG. 1 that extends from near the distal end 24 of the first clamping arm 12 towards the distal end 30 of the second clamping arm 14. In this exemplary embodiment, the ratchet toothed member 34 is attached to the distal end of that leg of the spring leg 32 that is fixed to the first clamping arm 12. It will be understood that the ratchet toothed member 34 may also be attached to the first clamping arm 12 directly.

The ratchet toothed member 34 has teeth facing in the direction towards the proximal end of the reduction clamp 10 and thereby provides a structure to engage the distal end 30 of the second clamping arm 14. Specifically, the teeth of the ratchet toothed member 34 permit to lock the position of the first and the second clamping arm 12 and 14 relative to one another so as to maintain a clamping force established between the tip portions 18 and 26. The bias of the leg spring 32 acts jointly with the ratchet toothed member 34 in that it forces the distal end 30 of the second clamping arm 14 into the teeth of the ratchet toothed member 34 and, thus, prevents the distal end 30 of the second clamping arm 14 from slipping out of the teeth of the ratchet toothed member 34 it engages with.

When the distal end 30 of the second clamping arm 14 is disengaged from the teeth of the ratchet toothed member 34 (e.g., by the operating surgeon), the bias provided by the leg spring 32 forces the distal ends 24 and 30 and, accordingly, the tip portions 18 and 26 away from each other unless the distal end 30 is engaged with (possibly other) teeth again. Thus, the bias force assists the operating surgeon in loosening the clamping arms 12 and 14 relative to one another when the distal end 30 is not engaged with the teeth of the ratchet toothed member 34. It will be understood, of course, that any other type of locking mechanism may be employed in order to lock the position of the first and the second clamping arm 12 and 14 of the reduction clamp 10 relative to one another so as to maintain a clamping force established between the tip portions 18 and 26.

The first and the second clamping arm 12 and 14 both exhibit a sequence of grooves 36 and 38 at outer surfaces of their distal ends 24 and 30. These grooves 36 and 38 define a hand grip portion that allows the operating surgeon to securely hold the reduction clamp 10.

Figure 2:
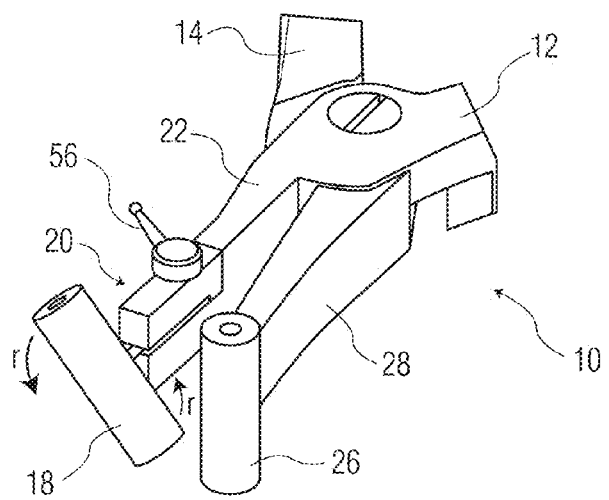
FIG. 2 shows a perspective view of a tip portion of the surgical reduction clamp of FIG. 1.

Referring now to FIG. 2, a perspective view of a proximal part of the surgical reduction clamp 10 is shown. This view particularly illustrates the specific movability of the tip portion 18 relative to the base portion 22 of the first clamping arm 12.

At the second clamping arm 14, the tip portion 26 is integrally joined to the base portion 28 and is thus in a rigid connection therewith. The sleeve representing the tip portion 26 is depicted in an upright position and is not movable relative to the base portion 28. The tip portion 18 of the first clamping arm 12, on the other hand, is coupled to the base portion 22 in a movable relationship by means of the joint 20. The sleeve representing the tip portion 18 is depicted in a slightly rotated position as compared to the upright position of the tip portion 26. The longitudinal axis of the sleeve extends substantially perpendicularly to the longitudinal axis of the base portion 22 indicated by line A-A in FIG. 1.

As indicated by arrows r, the tip portion 18 may be rotated about a longitudinal axis of the first clamping arm 12 (i.e., about the longitudinal axis indicated by line A-A in FIG. 1). A rotational movement of the tip portion 18 relative to the base portion 22 is thus allowed. The rotational direction indicated by arrows r in only one exemplary direction shall not be a limitation, and it will be understood that a rotational movement of the tip portion 18 in the opposite direction of the arrows r is allowed as well.

Figure 3:
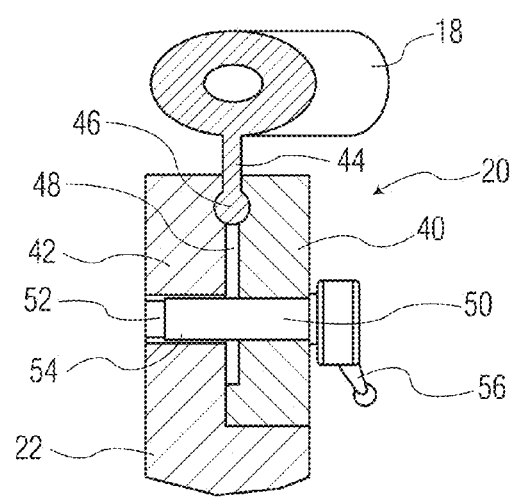
FIG. 3 shows a cross-sectional view along line A-A of the surgical reduction clamp of FIG. 1.

FIG. 3 shows a cross-sectional view of the surgical reduction clamp 10 along line A-A in FIG. 1 and illustrates in more detail how the coupling between the tip portion 18 and the base portion 22 is realized by means of the joint 20.

As shown in FIG. 3, the joint 20 comprises a bearing member 40, a proximal portion of the base portion 22 denoted as bearing base portion part 42, a cylindrical portion 44 of the tip portion 18 and a ball-shaped portion 46 of the tip portion 18. The ball-shaped portion 46 is adjacent to the cylindrical portion 44 and forms the distal end of the tip portion 18.

A clearance 48 is present between the bearing member 40 and the bearing base portion part 42 and the clearance 48 is dimensioned so as to receive the cylindrical portion 44 and the ball-shaped portion 46. For this purpose, a part of the clearance exhibits a cylindrical space formed by two opposing semi-cylindrical bearing recesses, one of which is formed in the bearing member 40 and one of which is formed in the bearing base portion part 42, for receiving the cylindrical portion 44. Distally adjacent to the cylindrical space, another part of the clearance 48 exhibits a spherical space formed by two opposing semi-spherical recesses, one of which is again formed in the bearing member 40 and one of which is again formed in the bearing base portion part 42, for receiving the ball-shaped portion 46.

The cylindrical space and the spherical space serve as a revolute bearing for the cylindrical portion 44 and the ball-shaped portion 46 and, thus, allow a rotational movement of the tip portion 18 relative to the base portion 22 only. The diameter of the ball-shaped portion 46 is generally greater than the diameter of the cylindrical space and, thus, the ball-shaped portion 46 is retained in the spherical space and may thus not inadvertently disengage from the joint 20.

A locking member 50 is disposed between the bearing member 40 and the bearing base portion part 42 and permits to pull the (moveable) bearing member 40 and the (stationary) bearing base portion part 42 together, thus reducing the clearance 48 and applying a clamping force on one or both of the cylindrical portion 44 and the ball-shaped portion 46. This clamping force fastens the position of the tip portion 18 relative to the base portion 22. The locking member 50 is realized by means of a screw-nut relationship as indicated by a screw 54 and a nut 52.

As long as the locking member 50 is not fully locked, the cylindrical portion 44 and the ball-shaped portion 46 are not clamped and are thus allowed to freely rotate about a longitudinal axis of the first clamping arm 12 as described above. As soon as the locking member 50 is fully locked, however, the cylindrical portion 44 and the ball-shaped portion 46 are clamped together and the rotational position of the tip portion 18 relative to the base portion 22 is fixed.

It will be understood that any other type of mechanism for pulling together the bearing member 40 and the bearing base portion part 42 may be employed. Also, the clamping structure does not necessarily have to be realized by clamping together the bearing member 40 and the bearing base portion part 42. Any other clamping structure which receives and fixes in a stationary manner a part of the tip portion may be implemented.

In order to eventually create the clamping force between the bearing member 40 and the bearing base portion part 42, the locking member 50 needs to be actuated. In this exemplary embodiment, the locking member 50 comprises a handle 56 for this purpose. The handle 56 may be turned and, thus, depending on the turning direction, will tighten or loosen the locking member 50. As mentioned above, the locking member 50 exhibits a screw-nut relationship and turning the handle 56 is therefore directly translated into a screwing action of the screw 54 in the nut 52.

The handle 56 provides a convenient means for the operating surgeon to lock or release the joint 20. Placing or turning the handle 56 into a locking position or direction may create the clamping force to lock the joint 20 and fasten the position of the tip portion 18. Placing or turning the handle 56 into a release position or direction may loosen the clamping force and release the joint 20 and, thus, allow for a rotational movement of the tip portion 18 relative to the base portion 22 again.

Instead of the handle 56, the locking member 50 may also comprise a screw head for actuating the locking member 50. In such an implementation, a separate tool (e.g., screw driver) may be provided for turning the locking member 50.

The coupling mechanism described above in conjunction with FIGS. 2 and 3 shall not limit the present disclosure. Various other embodiments of coupling a tip portion to a base portion are conceivable. Instead of allowing merely a rotational movement, the coupling mechanism may also be configured to allow a pivotable movement of the tip portion relative to the base portion. This may allow the tip portion to be pivoted about a pivot axis relative to the base portion. A pivoting and a rotational movement may also be combined. Such a behavior may be accomplished by coupling the tip portion to the base portion by means of a ball joint, for example.

Further, the coupling mechanism may generally allow for a configuration of the joint that permits the tip portion to be releasable from the base portion, thus, making the tip portion interchangeable. A sleeve tip may for example be exchanged by a another type of surgical instrument tip design. In the example illustrated in FIG. 3, the screw 54 may be fully disengaged from the nut 52 and the bearing member 40 may thus be fully detached from the bearing base portion part 42. In such a configuration the tip portion 18 may be replaced by another tip portion, before re-attaching the screw 54 together with the bearing member 40 in the nut 52 of the bearing base portion part 42.

Turning now to FIGS. 4a to 4d, variants of the surgical reduction clamp 10 with different configurations of the first and the second clamping arm 12 and 14 according to further embodiments of the present disclosure are shown.

Generally, the second clamping arm may, similar to the first clamping arm 12, also comprise a base portion, a tip portion, a joint movably coupling the tip portion to the base portion of the second clamping arm, and a locking member adapted to lock the joint so as to fasten a position of the tip portion relative to the base portion of the second clamping arm. The second clamping arm may even have the same configuration as the first clamping arm 12.

In the description of the exemplary variants shown in FIGS. 4a to 4d, the same reference numerals as previously used will be applied, but supplemented by a lower-case letter. Unless specifically noted in the following, reference is made to the above remarks for the purpose of describing the structural features denoted by the same reference numerals.

Figure 4A:
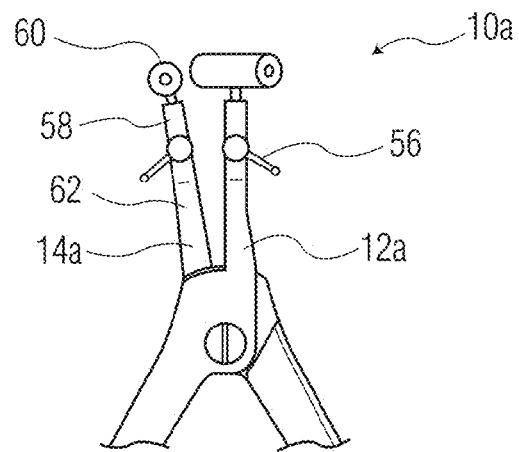
FIGS. 4a-d show variants of the surgical reduction clamp of FIG. 1 exhibiting different tip portion designs according to further embodiments of the present disclosure.

FIG. 4a depicts a surgical reduction clamp 10a with a first clamping arm 12a having the same configuration as the first clamping arm 12 described above. The second clamping arm 14a of the reduction clamp 10a exhibits the same configuration as the first clamping arm 12a and therefore comprises a joint 58 that allows a tip portion 60, here illustrated as a sleeve, to be adjusted in its rotational position relative to a base portion 62 of the second clamping arm 14a.

Figure 4B:
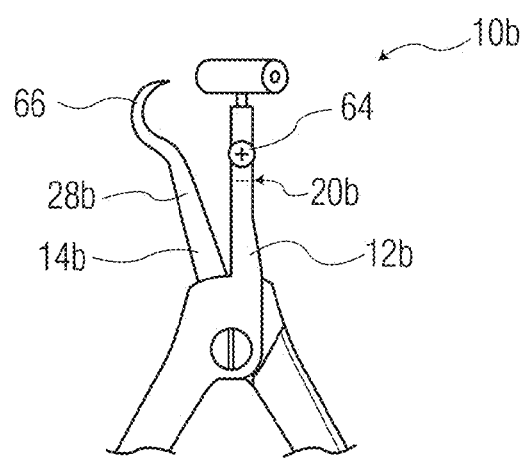

FIGS. 4b similarly shows a surgical reduction clamp 10b with a first clamping arm 12b having a configuration as the first clamping arm 12 described above, except that, instead of the handle 56, a screw head 64 is used to lock or release the joint 20b. The second clamping arm 14b, in the present embodiment, is realized as a tip portion 66 having a sharp bone tip which is integrally joined to the base portion 28b of the second clamping arm 14b. By employing sharp bone tips, the operating surgeon may be allowed to align fragments by gripping the bone, soft tissue structure or any other parts of the human anatomy.

Figure 4C:
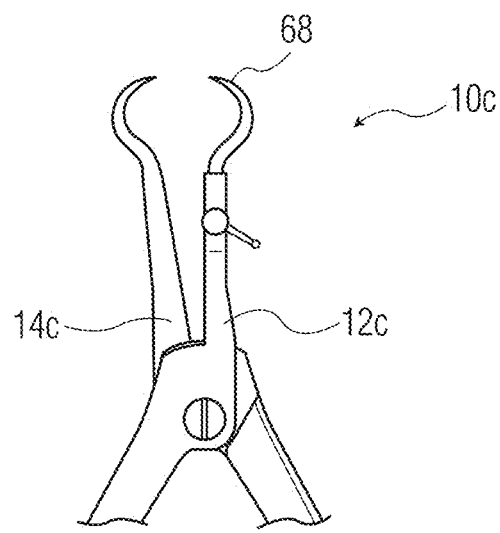

FIG. 4c shows a surgical reduction clamp 10c with a second clamping arm 14c having the same configuration as the second clamping arm 14b of FIG. 4b. The first clamping arm 12c differs from the first clamping 12b in that the tip portion 68 is given by a rotationally adjustable sharp bone tip.

Figure 4D:
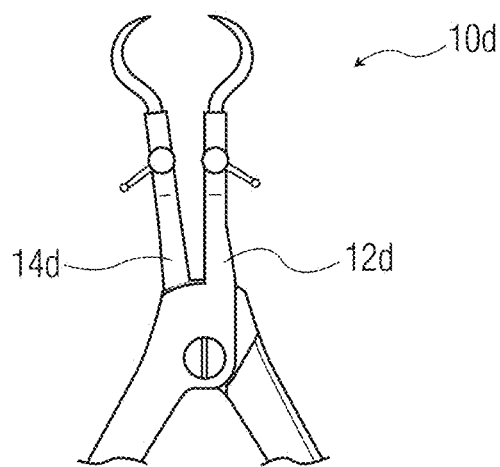

FIG. 4d shows a surgical reduction clamp 10d wherein both the first clamping arm 12d and the second clamping arm 14d exhibit the same adjustable configuration as the first clamping arm 12c of FIG. 4c.

It will be understood that FIGS. 4a to 4d only show examples of possible configuration options of the clamping arms. These and other manifold configuration options of the clamping arms, particularly their combined configuration variants, show that a highly versatile surgical instrument is provided which may be employed in a wide range of possible surgical applications.

While the present disclosure has been described with reference to exemplary embodiments, it will be appreciated that the present invention is not limited to what has been described above. Accordingly, it is intended that the present invention may be limited only by the scope of the claims appended hereto.

The invention claimed is:

1. A surgical reduction clamp comprising a first clamping arm and a second clamping arm movable relative to the first clamping arm, the first clamping arm comprising:
   a base portion;
   a tip portion;
   a joint movably coupling the tip portion of the first clamping arm to the base portion of the first clamping arm;
   a locking member adapted to lock the joint so as to fasten a position of the tip portion of the first clamping arm relative to the base portion of the first clamping arm;
   wherein the tip portion of the first clamping arm comprises a sleeve having a longitudinal axis substantially perpendicular to a longitudinal axis of the first clamping arm throughout an entire range of movement of the tip portion with respect to the longitudinal axis of the first clamping arm;
   wherein the second clamping arm comprises a base portion and a tip portion comprising an elongate member; and
   wherein the first and second clamping arm are pivotably coupled to one another.

2. The clamp according to claim 1, wherein the joint rotatably couples the tip portion of the first clamping arm to the base portion of the first clamping arm.

3. The clamp according to claim 2, wherein the tip portion of the first clamping arm is rotatable about a longitudinal axis of the first clamping arm.

4. The clamp according to claim 1, wherein the joint couples the tip portion of the first clamping arm to the base portion of the first clamping arm by means of a revolute joint.

5. The clamp according to claim 1, wherein the joint pivotably couples the tip portion of the first clamping arm to the base portion of the first clamping arm.

6. The clamp according to claim 1, wherein the locking member is adapted to lock the joint by applying a clamping force.

7. The clamp according to claim 1,
   wherein the locking member comprises a handle to lock or release the joint.

8. The clamp according to claim 1,
   wherein the locking member comprises a screw head to lock or release the joint.

9. The clamp according to claim 1,
   wherein the tip portion comprises a sharp bone tip.

10. The clamp according to claim 1, wherein the tip portion of the first clamping arm is releasable from the base portion of the first clamping arm and interchangeable.

11. The clamp according to claim 1, wherein a spring is formed between the first and the second clamping arm so as to bias the first and the second clamping arm relative to each other.

12. The clamp according to claim 1, wherein a ratchet toothed member is formed at one of the first and second clamping arm and extends towards the other clamping arm so as to permit locking of a position of the first and the second clamping arm relative to one another by engagement of the other clamping arm with teeth of the ratchet toothed member.

13. The clamp according to claim 1, wherein the tip portion of the second clamping arm is integrally joined to the second clamping arm.

14. The clamp according to claim 1, wherein the tip portion of the second clamping arm comprises a sleeve.

15. A surgical reduction clamp comprising a first clamping arm and a second clamping arm movable relative to the first clamping arm, the first clamping arm comprising:
   a base portion;
   a tip portion;

a joint movably coupling the tip portion of the first clamping arm to the base portion of the first clamping arm; and a locking member adapted to lock the joint so as to fasten a portion of the tip portion of the first clamping arm relative to the base portion of the first clamping arm, wherein the joint rotatably couples the tip portion of the first clamping arm to the base portion of the first clamping arm by means of a revolute joint, wherein the locking member is adapted to lock the revolute joint by applying a clamping force to a portion of the joint; and wherein the tip portion of the first clamping arm comprises a sleeve having a longitudinal axis substantially perpendicular to a longitudinal axis of the first clamping arm throughout an entire range of movement of the tip portion with respect to the longitudinal axis of the first clamping arm;

wherein the second clamping arm comprises a base portion and a tip portion comprising an elongate member; and wherein the first and second clamping arm are pivotably coupled to one another.

16. The clamp according to claim 15, wherein the tip portion of the first clamping arm has a cylindrical portion having a spherical end which spherical end portion forms part of the revolute joint.

* * * * *